(12) United States Patent
Thompson

(10) Patent No.: US 12,281,315 B1
(45) Date of Patent: Apr. 22, 2025

(54) COMPOSITION FOR REGULATING PRODUCTION OF PROTEINS

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/773,146

(22) Filed: Jul. 15, 2024

(51) Int. Cl.
 *C12N 15/67* (2006.01)
 *C07K 14/705* (2006.01)
 *C12N 15/86* (2006.01)
 *C12N 15/88* (2006.01)

(52) U.S. Cl.
 CPC ........ *C12N 15/67* (2013.01); *C07K 14/70596* (2013.01); *C12N 15/86* (2013.01); *C12N 15/88* (2013.01); *C12N 2750/14143* (2013.01)

(58) Field of Classification Search
 None
 See application file for complete search history.

(56) References Cited

U.S. PATENT DOCUMENTS

2020/0046809 A1* 2/2020 Thompson ............. A61K 38/46

* cited by examiner

*Primary Examiner* — Michael D Burkhart
(74) *Attorney, Agent, or Firm* — Gowling WLG (Canada) LLP

(57) ABSTRACT

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a protein, such as a toll-like receptor 9.

6 Claims, No Drawings

Specification includes a Sequence Listing.

SEQUENCE LISTING

```
Sequence total quantity: 3
SEQ ID NO: 1            moltype = DNA   length = 5194
FEATURE                 Location/Qualifiers
source                  1..5194
                        mol_type = other DNA
                        organism = synthetic construct
SEQUENCE: 1
ttctagaaag atctaacttg tttattgcag cttataatgg ttacaaataa agcaatagca   60
tcacaaattt cacaaataaa gcattttttt cactgcattc tagttgtggt ttgtccaaac  120
tcatcaatgt atcttatcat gtctggatct cgacctcgac tagagcatgg ctacgtagat  180
aagtagcatg gcgggttaat cattaactac aaggaacccc tagtgatgga gttggccact  240
ccctctctgc gcgctcgctc gctcactgag gccgggcgac caaaggtcgc ccgacgcccg  300
ggctttgccc gggcggcctc agtgagcgag cgagcgcgca gctggcgtaa tagcgaagag  360
gcccgcaccg atcgcccttc ccaacagttg cgcagcgtga atggcgaatg gcgattccgt  420
tgcaatggct ggcggtaata ttgttctgga tattaccagc aaggccgata gtttgagttc  480
ttctactcag gcaagtgatg ttattactaa tcaaagaagt attgcgacaa cggttaattt  540
gcgtgatgga cagactcttt tactcggtgg cctcactgat tataaaaaca cttctcagga  600
ttctggcgta ccgttcctgt ctaaaatccc tttaatcggc ctcctgttta gctcccgctc  660
tgattctaac gaggaaagca cgttatacgt gctcgtcaaa gcaaccatag tacgcgccct  720
gtagcggcgc attaagcgcg gcgggtgtgg tggttacgcg cagcgtgacc gctacacttg  780
ccagcgccct agcgcccgct cctttcgctt tcttcccttc ctttctcgcc acgttcgccg  840
gctttccccg tcaagctcta aatcggggc tccctttagg gttccgattt agtgctttac  900
ggcacctcga ccccaaaaaa cttgattagg gtgatggttc acgtagtggg ccatcgccct  960
gatagacggt ttttcgccct ttgacgttgg agtccacgtt ctttaatagt ggactcttgt 1020
tccaaactgg aacaacactc aacccctatct cggtctattc ttttgattta aagggatttt 1080
tgccgatttc ggcctattgg ttaaaaaatg agctgattta acaaaaattt aacgcgaatt 1140
ttaacaaaat attaacgttt acaatttaaa tatttgctta tacaatcttc ctgtttttgg 1200
ggcttttctg attatcaacc ggggtacata tgattgacat gctagtttta cgattaccgt 1260
tcatcgattc tcttgtttgc tccagactct caggcaatga cctgatagcc tttgtagaga 1320
cctctcaaaa atagctaccc tctccggcat gaatttatca gctagaacgg ttgaatatca 1380
tattgatggt gatttgactg tctccggcct ttctcacccg tttgaatctt tacctacaca 1440
ttactcaggc attgcattta aaatatatga gggttctaaa aattttttatc cttgcgttga 1500
aataaaggct tctcccgcaa aagtattaca gggtcataat gtttttggta caaccgattt 1560
agctttatgc tctgaggctt tattgcttaa ttttgctaat tctttgcctt gcctgtatga 1620
tttattggat gttggaattc ctgatgcggt attttctcct tacgcatctg tgcggtattt 1680
cacaccgcat atggtgcact ctcagtacaa tctgctctga tgccgcatag ttaagccagc 1740
cccgacaccc gccaacaccc gctgacgcgc cctgacgggc ttgtctgctc ccggcatccg 1800
cttacagaca agctgtgacc gtctccggga gctgcatgtg tcagaggttt tcaccgtcat 1860
caccgaaacg cgcgagacga aagggcctcg tgatacgcct atttttatag gttaatgtca 1920
tgataataat ggtttcttag acgtcaggtg gcacttttcg gggaaatgtg cgcggaaccc 1980
ctatttgttt atttttctaa atacattcaa atatgtatcc gctcatgaga caataaccct 2040
gataaatgct tcaataatat tgaaaaagga agagtatgag tattcaacat ttccgtgtcg 2100
cccttattcc cttttttgcg gcattttgcc ttcctgtttt tgctcaccca gaaacgctgg 2160
tgaaagtaaa agatgctgaa gatcagttgg gtgcacgagt gggttacatc gaactggatc 2220
tcaacagcgg taagatcctt gagagttttc gccccgaaga acgttttcca atgatgagca 2280
cttttaaagt tctgctatgt ggcgcggtat tatcccgtat tgacgccggg caagagcaac 2340
tcggtcgccg catacactat tctcagaatg acttggttga gtactcacca gtcacagaaa 2400
agcatcttac ggatggcatg acagtaagag aattatgcag tgctgccata accatgagtg 2460
ataacactgc ggccaactta cttctgacaa cgatcggagg accgaaggag ctaaccgctt 2520
ttttgcacaa catgggggat catgtaactc gccttgatcg ttgggaaccg gagctgaatg 2580
aagccatacc aaacgacgag cgtgacacca cgatgcctgt agcaatggca acaacgttgc 2640
gcaaactatt aactggcgaa ctacttactc tagcttcccg gcaacaatta atagactgga 2700
tggaggcgga taaagttgca ggaccacttc tgcgctcggc ccttccggct ggctggttta 2760
ttgctgataa atctggagcc ggtgagcgtg ggtctcgcgg tatcattgca gcactggggc 2820
cagatggtaa gccctcccgt atcgtagtta tctacacgac ggggagtcag gcaactatgg 2880
atgaacgaaa tagacagatc gctgagatag gtgcctcact gattaagcat tggtaactgt 2940
cagaccaagt ttactcatat atactttaga ttgatttaaa acttcatttt taatttaaaa 3000
ggatctaggt gaagatcctt tttgataatc tcatgaccaa aatcccttaa cgtgagtttt 3060
cgttccactg agcgtcagac cccgtagaaa agatcaaagg atcttcttga gatccttttt 3120
ttctgcgcgt aatctgctgc ttgcaaacaa aaaaaccacc gctaccagcg gtggtttgtt 3180
tgccggatca gagctacca actctttttc cgaaggtaac tggcttcagc agagcgcaga 3240
taccaaatac tgtccttcta gtgtagccgt agttaggcca ccacttcaag aactctgtag 3300
caccgcctac atacctcgct ctgctaatcc tgttaccagt ggctgctgcc agtggcgata 3360
agtcgtgtct taccgggttg gactcaagac gatagttacc ggataaggcg cagcggtcgg 3420
```

```
gctgaacggg gggttcgtgc acacagccca gcttggagcg aacgacctac accgaactga  3480
gatacctaca gcgtgagcta tgagaaagcg ccacgcttcc cgaagggaga aaggcggaca  3540
ggtatccggt aagcggcagg gtcggaacag gagagcgcac gagggagctt ccaggggga   3600
acgcctggta tctttatagt cctgtcgggt ttcgccacct ctgacttgag cgtcgatttt  3660
tgtgatgctc gtcaggggg  cggagcctat ggaaaaacgc cagcaacgcg gccttttac   3720
ggttcctggc cttttgctgg ccttttgctc acatgttctt tcctgcgtta tcccctgatt  3780
ctgtggataa ccgtattacc gcctttgagt gagctgatac cgctcgccgc agccgaacga  3840
ccgagcgcag cgagtcagtg agcgaggaag cggaagagcg cccaatacgc aaaccgcctc  3900
tccccgcgcg ttggccgatt cattaatgca gctgcgcgct cgctcgctca ctgaggccgc  3960
ccgggcaaag cccgggcgtc gggcgacctt tggtcgcccg gcctcagtga gcgagcgagc  4020
gcgcagagag ggagtggcca actccatcac taggggttcc ttgtagttaa tgattaaccc  4080
gccatgctac ttatctacgt agccatgctc taggacattg attattgact agtggagttc  4140
cgcgttacat aacttacggt aaatggcccg cctggctgac cgcccaacga cccccgccca  4200
ttgacgtcaa taatgacgta tgttcccata gtaacgccaa tagggactttt ccattgacgt  4260
caatgggtgg agtatttacg gtaaactgcc cacttggcag tacatcaagt gtatcatatg  4320
ccaagtacgc ccctattga cgtcaatgac ggtaaatggc ccgcctggca ttatgcccag  4380
tacatgacct tatgggactt tcctacttgg cagtacatct acgtattagt catcgctatt  4440
accatggtcg aggtgagccc cacgttctgc ttcactctcc ccatctcccc ccctcccca   4500
cccccaattt tgtatttatt tatttttaa ttattttgtg cagcgatggg gcgggggg     4560
gggggggggcg cgcgccaggc ggggcgggggc ggggcgaggg gcgggggcggg gcgaggcgga  4620
gaggtgcggc ggcagccaat cagagcggcg cgctccgaaa gtttccttt atggcgaggc  4680
ggcggcggcg gcggccctat aaaaagcgaa gcgcgcggcg ggcgggagtc gctggcgct   4740
gccttcgccc cgtgccccgc tccgccgccg cctcgcgccg cccgcccgg ctctgactga   4800
ccgcgttact aaaacaggta agtccggcct ccgcgccggg ttttggcgcc tcccgcgggc  4860
gccccctcc tcacgcgag cgctgccacg tcagacgaag ggcgcagcga cgtcctgat    4920
ccttccgccc ggacgctcag gacagcggcc cgctgctcat aagactcggc cttagaaccc  4980
cagtatcagc agaaggacat tttaggacgg gacttgggtg actctagggc actggttttc  5040
tttccagaga gcgaacagg  cgaggaaaag tagtccccttc tcggcgattc tgcggaggga  5100
tctccgtggg gcggtgaacg ccgatgatgc ctctactaac catgttcatg tttttctttt  5160
ttttctacag gtcctgggtg acgaacaggg tacc                              5194

SEQ ID NO: 2        moltype = DNA  length = 3105
FEATURE             Location/Qualifiers
source              1..3105
                    mol_type = other DNA
                    organism = synthetic construct
SEQUENCE: 2
gccaccatgg gcttctgcag aagcgccttg caccctctga gtctcctggt gcaggctatc  60
atgctggcca tgacccttgc cctgggcaca ctgccagctt tcttgccttg cgagctgcag  120
cctcacggac tggtcaactg taattggctg ttcctgaaga gcgtgcctca cttttctatg  180
gccgcccta  gaggcaacgt gacatctcta agcctgagca gcaacggat  tcaccatctg  240
cacgacagcg acttcgccca cctgccttct ctgcgccact gaacctgaa  atggaactgc  300
ccccccgtgg gcctgagccc aatgcacttt cctttgtcact tgaccatcga acctagcagc  360
ttctctggct tcctaccct ggaagaactg aacctgagct acaataacat catgacagtg  420
cctgccctgc caaagagcct gatcagcctg tccttatctc acaccaacat cctgatgcta  480
gatagcgcta gcctggctgg actgcatgcc ctgagattcc tgttcatgga cggcaactgc  540
tactacaaga accccctgtag acaggcactg gaggtgccc  ctggagcccc gctgggcctt  600
ggcaatctga cccacctgag cctgaagtac aacaacctga cagtggtgcc tcggaatctc  660
cccagctccc ttgagtacct gctcctgagc tacaacagaa tcgtgaagtt ggcccctgag  720
gatctggcca accttaccgc cctgcggtgt ctggacgtgg aggcaactg cagacggtgc  780
gaccagccc  ctaaccctgg catggaatgc cctagacact tcccccagct gcaccctgac  840
acattcagcc atctgagcag actggaaggc ctggtgctga aggacagcag cctgtcttgg  900
ctgaacgcca gctggttcag aggactcggc aacctgcggg ttctggatct gagcgagaac  960
ttcctgtata aatgcatcac caagaccaag gcctttcagg gcctgacaca gctgagaaag  1020
ctgaacctga gcttcaacta ccagaaaaga gtgagctttg cccacctgtc cctggcgcct  1080
tcctttggct ctctggtggc cctgaaagaa ctggacatgc acggcatctt cttcagaagc  1140
ctcgatgaaa ccaccctgag acctctgca  agactgccca tgctgcaaac actgaggctg  1200
cagatgaact tcatcaacca ggctcagctg ggaatcttca gagccttccc cggcctcaga  1260
tacgtggacc tgagtgacaa ccggatcagc ggcgcctccg agctgaccgc caccatggga  1320
gaagccgatg gcgcgaagc  ggtgtgggctg cagcctggcg atttggctcc tgccctgtg   1380
gacaccccaa gctctgagga ttttcgacct aattgcagca ccctgaactt caccctggac  1440
cttttctcgga caaacctggt tacagtgcaa cctgaaatgt tcgcccagct gagccacctg  1500
cagtgcctgc ggctgagcca caattgtatc agccaggctg tgaacggttc ccaatttctg  1560
ccactgaccg gcctgcaggt gctggatctc tctcacaata gctggatcta gtaccacgag  1620
cacagcttta cagagctacc ccggctgagg gccctggatc tgagctataa cagccaacct  1680
ttcggcatgc agggcgtggg ccacaacttc tctttcgtgg cccacctgag aaccctgaga  1740
cacttatccc tggctcataa caacatccac agccaggtgt cccaacagct gtgcagcaca  1800
tccctcagag ccctggactt tccggcaac  gcctaggtc atatgtgggc cgagggcgat  1860
ctgtacctgc acttcttcca gggctgagc  gggctgatct ggggacttt  aagccagaac  1920
agactgcaca cactgctgcc acagaccctg agaaacctgc ctaagtccct gcaggtcctt  1980
aggctgagag acaattacct ggcattcttc aagtggtggt ccctccactt cctgcccaag  2040
ctggaggttc tcgacctggc cggcaaccag ctgaaagccc tgaccaacgg cagcctgccc  2100
gctggcacca gactgcggcg gctcgacgtg agctgcaaca gtatttcttt cgtggccccc  2160
ggattcttta gcaaggcaa agagctgagg gaactgaatc tgtctgccaa cgctgtcgaag  2220
accgttgatc acagctggtt cggacctctg gccagcgccc tgcaaatcct ggacgtgagc  2280
gccaatcccc ttcactgcgc ctgcggcgcc gcatttatgg acttcctact ggaggtgcag  2340
gccgccgtgc ctgccttcc  tagcggggtc aagtgcggca gccctggcca gctgcaagga  2400
ctctccatct tcgctcagga cctgcgcctg tgtctgacg  aggccctgtc ttgggattgc  2460
ttcgccctgt cactgctggc ggtggccctg ggcctggggc tgcccatgct gcatcacctg  2520
```

```
tgtggttggg acctgtggta ctgcttccac ctgtgcctcg cttggctgcc ttggcgggga    2580
agacagagcg gcagagacga ggacgccctg ccatacgacg cctttgtggt gttcgacaag    2640
acccagagcg ccgtggccga ctgggtgtat aacgagctga ggggccagct cgaagagtgt    2700
agaggccggt gggctctgcg tctgtgcctt gaggaaagag actggctgcc cggcaagaca    2760
cttttcgaga acttgtgggc cagcgtgtac ggcagcagaa agaccctgtt cgtgctggcc    2820
cacactgata gagtgagcgg cctgctgcgg gccagctttc tgctcgctca gcagcggctg    2880
ctggaagaca gaaaggacgt ggttgtgctt gtgatcctga gccctgacgg cagaagaagc    2940
cggtacgtgc ggctgagaca gagactgtgt agacagtctg tgttgctgtg gccccaccag    3000
cccagcggac agagatcctt ctgggcccaa ctgggcatgg ctctgaccag agataaccac    3060
cacttctaca accggaattt ctgccagggc cctacagccg agtga                   3105

SEQ ID NO: 3              moltype = DNA   length = 8299
FEATURE                   Location/Qualifiers
source                    1..8299
                          mol_type = other DNA
                          organism = synthetic construct
SEQUENCE: 3
ttctagaaag atctaacttg tttattgcag cttataatgg ttacaaataa agcaatagca     60
tcacaaattt cacaaataaa gcatttttt cactgcattc tagttgtggt ttgtccaaac    120
tcatcaatgt atcttatcat gtctggatct cgacctcgac tagagcatgg ctacgtagat    180
aagtagcatg gcgggttaat cattaactac aaggaacccc tagtgatgga gttggccact    240
ccctctctgc gcgctcgctc gctcactgag gccggggcac caaaggtcgc cgacgccgg    300
ggctttgccc gggcggcctc agtgagcgag cgagcgcgca gctggcgtaa tagcgaagag    360
gcccgcaccg atcgcccttc ccaacagttg cgcagcctga atggcgaatg gcgattccgt    420
tgcaatggct ggcggtaata ttgttctgga tattaccagc aaggccgata gtttgagttc    480
ttctactcag gcaagtgatg ttattactaa tcaaagaagt attgcgacaa cggttaattt    540
gcgtgatgga cagactcttt tactcggtgg cctcactgat tataaaaaca cttctcagga    600
ttctggcgta ccgttcctgt ctaaaatccc tttaatcggc ctcctgttta gctcccgctc    660
tgattctaac gaggaaagca cgttatacgt gctcgtcaaa gcaaccatag tacgcgcccc    720
gtagcggcgc attaagcgcg gcgggtgtgg tggttacgcg cagcgtgacc gctacacttg    780
ccagcgccct agcgcccgct cctttcgctt tcttccctc ctttctcgcc acgttcgccg    840
gctttccccg tcaagctcta aatcgggggc tccctttagg gttccgattt agtgctttac    900
ggcacctcga ccccaaaaaa cttgattagg gtgatggttc acgtagtggg ccatcgccct    960
gatagacggt ttttcgccct ttgacgttgg agtccacgtt ctttaatagt ggactcttgt   1020
tccaaactgg aacaacactc aaccctatct cggtctattc ttttgattta agggatttt   1080
tgccgatttc ggcctattgg ttaaaaaatg agctgattta acaaaaattt aacgcgaatt   1140
ttaacaaaat attaacgttt acaatttaaa tatttgctta caatccttc ctgttttgg   1200
gcttttctg attatcaacc ggggtacata tgattgacat gctagtttta cgattaccgt   1260
tcatcgattc tcttgtttgc tccagactct caggcaatga cctgatagcc tttgtagaga   1320
cctctcaaaa atagctaccc tctccggcat gaatttatca gctagaacgg ttgaatatca   1380
tattgatggt gatttgactg tctccggcct ttctcacccg tttaatcttt acctacaca   1440
ttactcaggc attgcatta aaatatatga gggttctaaa aatttttatc cttgcgttga   1500
aataaaggct tctcccgcaa aagtattaca gggtcataat gtttttggta caaccgattt   1560
agctttatgc tctgaggctt tattgcttaa ttttgctaat tcttttgcctt gcctgtatga   1620
tttattggat gttggaattc ctgatgcgg atttttctcct tacgcatctg tgcggtattt   1680
cacaccgcat atggtgcact ctcagtacaa tctgctctga tgccgcatag ttaagccagc   1740
cccgacaccc gccaacaccc gctgacgcgc cctgacgggc ttgtctgctc ccggcatccg   1800
cttacagaca agctgtgacc gtctccggga gctgcatgtg tcagaggttt tcaccgtcat   1860
caccgaaacg cgcgagacga aggggcctcg tgatacgcct atttttatag gttaatgtca   1920
tgataataat ggtttcttag acgtcaggtg gcacttttcg gggaaatgtg cgcggaaccc   1980
ctatttgttt atttttctaa atacattcaa atatgtatcc gctcatgaga caataaccct   2040
gataaatgct tcaataatat tgaaaaagga agagtatgag tattcaacat ttccgtgtcg   2100
cccttattcc cttttttgcg cattttgcc ttcctgtttt tgctcaccca gaaacgctgg   2160
tgaaagtaaa agatgctgaa gatcagttgg gtgcacgagt gggttacatc gaactggatc   2220
tcaacagcgg taagatcctt gagagttttc gccccgaaga acgttttcca atgatgagca   2280
cttttaaagt tctgctatgt ggcgcggtat tatcccgtat tgacgccggg caagagcaac   2340
tcggtcgccg catacactat tctcagaatg acttggttga gtactcacca gtcacagaaa   2400
agcatcttac ggatggcatg acagtaagag aattatgcag tgctgccata accatgagtg   2460
ataacactgc ggccaactta cttctgacaa cgatcggagg accgaaggag ctaaccgctt   2520
ttttgcacaa catgggggat catgtaactc gccttgatcg ttgggaaccg gagctgaatg   2580
aagccatacc aaacgacgag cgtgacacca cgatgcctgt agcaatggca acaacgttgc   2640
gcaaactatt aactggcgaa ctacttactc tagcttcccg gcaacaatta atagactgga   2700
tggaggcgga taaagttgca ggaccacttc tgcgctcggc ccttccggct ggctggttta   2760
ttgctgataa atctggagcc ggtgagcgtg ggtctcgcgg tatcattgca gcactggggc   2820
cagatggtaa gccctcccgt atcgtagtta tctacacgac ggggagtcag gcaactatgg   2880
atgaacgaaa tagacagatc gctgagatag gtgcctcact gattaagcat tggtaactgt   2940
cagaccaagt ttactcatat atactttaga ttgatttaaa acttcatttt taatttaaaa   3000
ggatctaggt gaagatcctt tttgataatc tcatgaccaa aatcccttaa cgtgagtttt   3060
cgttccactg agcgtcagac cccgtagaaa agatcaaagg atcttcttga gatcctttt   3120
ttctgcgcgt aatctgctgc ttgcaaacaa aaaaaccacc gctaccagcg gtggtttgtt   3180
tgccggatca agagctacca actctttttc cgaaggtaac tggcttcagc agagcgcaga   3240
taccaaatac tgtccttcta gtgtagccgt agttaggcca ccacttcaag aactctgtag   3300
caccgcctac atacctcgct ctgctaatcc tgttaccagt ggctgctgcc agtggcgata   3360
agtcgtgtct taccgggttg gactcaagac gatagttacc ggataaggcg cagcggtcgg   3420
gctgaacggg gggttcgtgc acacagccca gcttggagcg aacgacctac accgaactga   3480
gatacctaca gcgtgagcta tgagaaagcg ccacgcttcc cgaagggaga aaggcggaca   3540
ggtatccggt aagcggcagg gtcggaacag gagagcgcac gagggagctt ccagggggaa   3600
acgcctggta tctttatagt cctgtcgggt ttcgccacct ctgacttgag cgtcgatttt   3660
tgtgatgctc gtcagggggg cggagcctat ggaaaaacgc cagcaacgcg gcctttttac   3720
```

```
ggttcctggc cttttgctgg ccttttgctc acatgttctt tcctgcgtta tccctgatt   3780
ctgtggataa ccgtattacc gcctttgagt gagctgatac cgctcgccgc agccgaacga   3840
ccgagcgcag cgagtcagtg agcgaggaag cggaagagcg cccaatacgc aaaccgcctc   3900
tccccgcgcg ttggccgatt cattaatgca gctgcgcgct cgctcgctca ctgaggccga   3960
ccgggcaaag cccgggcgtc gggcgacctt tggtcgcccg gcctcagtga gcgagcgagc   4020
gcgcagagag ggagtggcca actccatcac taggggttcc ttgtagttaa tgattaaccc   4080
gccatgctac ttatctacgt agccatgctc taggacattg attattgact agtgagttc   4140
cgcgttacat aacttacggt aaatggcccg cctggctgac cgcccaacga cccccgccca   4200
ttgacgtcaa taatgacgta tgttcccata gtaacgccaa tagggacttt ccattgacgt   4260
caatgggtgg agtatttacg gtaaactgcc cacttggcag tacatcaagt gtatcatatg   4320
ccaagtacgc ccctattga cgtcaatgac ggtaaatggc ccgcctggca ttatgcccag   4380
tacatgacct tatgggactt tcctacttgg cagtacatct acgtattagt catcgctatt   4440
accatggtcg aggtgagccc cacgttctgc ttcactctcc ccatctcccc ccctcccca   4500
cccccaattt tgtatttatt tattttttaa ttattttgtg cagcgatgg ggcggggggg   4560
ggggggggcg cgcgccaggc ggggcgggggc ggggcgaggg gcgggcgggg gcgaggcgga   4620
gaggtgcggc ggcagccaat cagagcggcg cgctccgaaa gtttccttt atggcgaggc   4680
ggcggcggcg gcggccctat aaaaagcgaa gcgcgcggcg ggcgggagtc gctgcgcgct   4740
gccttcgccc cgtgccccgc tccgccgccg cctcgcgccg cccccgcccc gg ctctgactga   4800
ccgcgttact aaaacaggta agtccggcct ccgcgccggg ttttggcgcc tcccgcgggc   4860
gcccccctcc tcacggcgag cgctgccacg tcagacgaag ggcgcagcga gcgtcctgat   4920
ccttccgccc ggacgctcag gacagcggcc cgctgctcat aagactcggc cttagaaccc   4980
cagtatcagc agaaggacat tttaggacgg gacttgggtg actctagggc actgttttc   5040
tttccagaga gcggaacagg cgaggaaaag tagtccccttc tcggcgattc tgcggaggga   5100
tctccgtggg gcggtgaacg ccgatgatgc ctctactaac catgttcatg ttttctttt   5160
ttttctacag gtcctgggtg acgaacaggg taccgccacc atgggcttct gcagaagcgc   5220
cttgcaccct ctgagtctcc tggtgcaggc tatcatgcct gccatgaccc ttgcctggga   5280
cacactgcca gctttcttgc cttgcgagct gcagcctcac ggactggtca actgtaattg   5340
gctgttcctg aagagcgtgc ctcacttttc tatggccgcc cctagaggca acgtgacatc   5400
tctaagcctg agcagcaacc ggattcacca tctgcacgac agcgacttcg cccacctgcc   5460
ttctctgcgc cacttgaacc tgaaatgaa ctgccccccc gtgggcctga gcccaatgca   5520
cttttcctgt cacatgacca tcgaacctag cacccttctg gctgttccta ccctggaaga   5580
actgaacctg agctacaata acatcatgac agtgcctgcc ctgccaaaga gcctgatcag   5640
cctgtcctta tctcacacca acatcctgat gctagatagc gctagcctgg ctggactgca   5700
tgccctgaga ttcctgttca tggacggcaa ctgctactac aagaaccct gtagacaggc   5760
actggaggtg gccctggag ccctgctggg ccttggcaat ctgacccacc tgagcctgaa   5820
gtacaacaac ctgacagtgg tgcctcgaa tctccccagc tcccttgagt acctgctcct   5880
gagctacaac agaatcgtga agttggcccc tgaggatctg gccaacctta ccgccctgcg   5940
ggtgctggac gtgggaggca actgcagacg gtgcgaccac gcccctaacc cttgcatgga   6000
atgccctaga cacttccccc agctgcaccc tgacacattc agccatctga gcagactgga   6060
aggcctggtg ctgaaggaca gcagcctgtc ttggctgaac gccagctggt tcagaggact   6120
cggcaacctg cgggttctgg atctgagcga aacttcctg tataaatgca tcaccaagac   6180
caaggccttt cagggcctga cacagctgag aaagctgaac ctgagcttca actaccagaa   6240
aagagtgac tttgcccacc tgtccctggc ccttcctt ggctctctgg tggcctgaa   6300
agaactggac atgcacggca tcttcttcag aagcctcgat gaaaccaccc tgagacctct   6360
cgcaagactg cccatgctgc aaacactgag gctgcagatg aacttcatca accaggctca   6420
gctgggaatc ttcagagcct tccccggcct cagatacgtg gacctgagtg acaaccggat   6480
cagcggcgcc tccgagctga ccgccaccat gggagaagcc gatggcggcg agaaggtgtg   6540
gctgcagcct ggcgatttgg ctcctgcccc tgtggacacc ccaagctctg aggattttcg   6600
acctaattgc agcaccctga acttcaccct ggaccttct cggaacaacc tggttacagt   6660
gcaacctgaa atgttcgccc agctgagcca cctgcagtgc ctgcggctga ccacaattg   6720
tatcacgcag gctgtgaacg gttcccaatt tctgccactg accggcctgc aggtgctgga   6780
tctctctcac aataagctgg atctgtacca cgagcacagc tttacagagc tacccggct   6840
ggaggccctg gatctgagct ataacagcca acctttcggc atgcagggcg tgggccacaa   6900
cttctctttc gtgccccacc tgagaaccct gagacactta tccctggctc ataacaacat   6960
ccacagccag gtgtcccaac agctgtgcag cacatcccta agagccctgg acttctccgg   7020
caacgcctta ggtcatatgt gggccgaggg cgatctgtac ctgcacttct tccagggcct   7080
gagcgggctg atctggctgg acttaagcca gaacagactg cacacactgc tgccacagac   7140
cctgagaaac ctgcctaagt ccctgcaggt ccttaggctg agagacaatt acctggcatt   7200
cttcaagtgg tggtccctcc acttcctgcc caagctggag gttctcgacc tggccggcaa   7260
ccagctgaaa gccctgacca acggcagcct gccggctgc accagactgc ggcggctcga   7320
cgtgagctgc aacagtattt ctttcgtggc cccggattc tttagcaagg ccaaagagct   7380
gagggaactg aatctgtctg ccaacgccct gaagaccgtt gatcacagct ggttcggacc   7440
tctggccagc gccctgcaaa tcctggacgt gagcgccaat ccccttcact cgcctgcgg   7500
cgccgcattt atggacttcc tactggaggt gcaggccgc gtgcctggcc ttcctagccg   7560
ggtcaagtgc ggcagccctg gccagctgca aggactctcc atcttcgctc aggacctgcg   7620
cctgtgtctg gacgaggccc tgtcttggga ttgcttcgcc ctgtcactgc tggcggtggc   7680
cctgggcctg ggcgtgccca tgctgcatca cctgtgtggt tgggacctgt ggtactgctt   7740
ccacctgtgc ctcgcttggc tgccttggcg gggaagacag agcggcagag acgaggacgc   7800
cctgccatac gacgcctttg tggtgttcga caagacccag agcgccgtgg ccgactgggt   7860
gtataacgag ctgaggggcc agctcgaaga gtgtagaggc cggtgctcc tgcgtctgta   7920
ccttgaggaa agagactggc tgccggcaa gacactttc gagaacttgt gggcagcgt   7980
gtacggcagc agaaagaccc tgttcgtgct ggcccacact gatagagtga gcggcctgct   8040
gcgggccagc tttctgctcg ctcagcagcg gctgctggaa gacagaaagg acgtggttgt   8100
gcttgtgatc ctgagccctg acggcagaag aagccggtac gtgcggctga gacagagact   8160
gtgtagacag tctgtgttgc tgtggcccca ccagcccagc ggacagagat ccttctggc   8220
ccaactgggc atggctctga ccagagataa ccaccacttc tacaaccgga atttctgcca   8280
gggccctaca gccgagtga                                                 8299
```

COMPOSITION FOR REGULATING PRODUCTION OF PROTEINS

This application contains a Sequence Listing electronically submitted via Patent Center to the United States Patent and Trademark Office as an XML Document file entitled "A8149590US-Sequence Listing ST26.xml" created on 2024 Jul. 15 and having a size of 19,824 bytes. The information contained in the Sequence Listing is incorporated by reference herein.

TECHNICAL FIELD

The present disclosure generally relates to compositions for regulating the production of proteins. In particular, the present disclosure relates to compositions for regulating gene expression and consequently, the production, of proteins.

BACKGROUND

Bioactive molecules, including toll-like receptors, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address the losses of homeostasis and the regulation of bioactive molecules in order to prevent or treat the resulting disease.

SUMMARY

Some embodiments of the present disclosure relate to one or more compositions that upregulate the production of one or more sequences of mRNA. The sequences of mRNA may encode for translation of a target biomolecule, thereby causing an increase in bioavailability of the target biomolecule within a subject that is administered the one or more compositions. In some embodiments of the present disclosure, the target biomolecule is a protein, such as toll-like receptor 9 (TLR9).

In some embodiments of the present disclosure the compositions comprise a plasmid of deoxyribonucleic acid (DNA) that includes one or more insert sequences of nucleic acids that encode for the production of mRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the mRNA and, consequently, increased translation of the target biomolecule by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding an mRNA sequence that encodes for the protein TLR9.

Some embodiments of the present disclosure relate to a method of making a composition/target cell complex. The method comprising a step of administering an RP comprising SEQ ID NO. 1 and SEQ ID NO. 2 to a target cell for forming the composition/target cell complex, wherein the composition/target cell complex causes the target cell to increase production of one or more sequences of mRNA that increases production of a target biomolecule.

Embodiments of the present disclosure relate to at least one approach for inducing endogenous production of one or more sequences of mRNA that encodes for a target biomolecule, for example TLR9. A first approach utilizes gene vectors containing nucleotide sequences for increasing the endogenous production of one or more sequences of mRNA, which are complete or partial sequences and/or combinations thereof of TLR9, which can be administered to a subject to increase the subject's production of one or more sequences of the mRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject. A biomolecule may be endogenous or exogenous to a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus vector.

In some embodiments of the present disclosure, the insert comprises one or more nucleotide sequences that encode for production of at least one sequence of mRNA that increases the production of target biomolecules, such as a protein.

In some embodiments of the present disclosure, the target biomolecule is TLR9.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy. The gene therapy is useful for increasing the subject's endogenous production of one or more sequences of mRNA that encode for a target biomolecule. For example, the RP can contain one or more nucleotide sequences that cause increased production of one or more nucleotide sequences that cause an increased production of one or more mRNA sequences that encode for one or more biomolecules, such as TLR9.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass). In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments of the present disclosure, the therapeutically effective amount of the composition is between about 10 and about $1 \times 10^{16}$ TCP/kg.

Some embodiments of the present disclosure relate to an adeno-associated virus (AAV) genome consisting of an RP that when operable inside a target cell will cause the target cell to produce a mRNA sequence that upregulates production of a biomolecule, with an example being TLR9. The RP is comprised of AAV2 inverted terminal repeats (ITRs), a composite CASI promoter, and a human growth hormone (HGH) signal peptide followed by a mRNA expression cassette encoding for TLR9, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):

TTCTAGAAAGATCTAACTTGTTTATTGCAGCTTATAATGGTTACAAATAAAGCAATA

GCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCT

ACGTAGATAAGTAGCATGGCGGGTTAATCATTAACTACAAGGAACCCCTAGTGATG

GAGTTGGCCACTCCCTCTCTGCGCGCTCGCTCGCTCACTGAGGCCGGGCGACCAAAG

GTCGCCCGACGCCCGGGCTTTGCCCGGGCGGCCTCAGTGAGCGAGCGAGCGCGCAG

CTGGCGTAATAGCGAAGAGGCCCGCACCGATCGCCCTTCCCAACAGTTGCGCAGCC

TGAATGGCGAATGGCGATTCCGTTGCAATGGCTGGCGGTAATATTGTTCTGGATATT

ACCAGCAAGGCCGATAGTTTGAGTTCTTCTACTCAGGCAAGTGATGTTATTACTAAT

CAAAGAAGTATTGCGACAACGGTTAATTTGCGTGATGGACAGACTCTTTTACTCGGT

GGCCTCACTGATTATAAAAACACTTCTCAGGATTCTGGCGTACCGTTCCTGTCTAAA

ATCCCTTTAATCGGCCTCCTGTTTAGCTCCCGCTCTGATTCTAACGAGGAAAGCACGT

TATACGTGCTCGTCAAAGCAACCATAGTACGCGCCCTGTAGCGGCGCATTAAGCGC

GGCGGGTGTGGTGGTTACGCGCAGCGTGACCGCTACACTTGCCAGCGCCCTAGCGC

CCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACG

GTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAATTT

TAACAAAATATTAACGTTTACAATTTAAATATTTGCTTATACAATCTTCCTGTTTTTG

GGGCTTTTCTGATTATCAACCGGGGTACATATGATTGACATGCTAGTTTTACGATTAC

CGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTT

GAATATCATATTGATGGTGATTTGACTGTCTCCGGCCTTTCTCACCCGTTTGAATCTT

TACCTACACATTACTCAGGCATTGCATTTAAAATATATGAGGGTTCTAAAAATTTTT

ATCCTTGCGTTGAAATAAAGGCTTCTCCCGCAAAAGTATTACAGGGTCATAATGTTT

TTGGTACAACCGATTTAGCTTTATGCTCTGAGGCTTTATTGCTTAATTTTGCTAATTC

-continued

```
TTTGCCTTGCCTGTATGATTTATTGGATGTTGGAATTCCTGATGCGGTATTTTCTCCTT

ACGCATCTGTGCGGTATTTCACACCGCATATGGTGCACTCTCAGTACAATCTGCTCT

GATGCCGCATAGTTAAGCCAGCCCCGACACCCGCCAACACCCGCTGACGCGCCCTG

ACGGGCTTGTCTGCTCCCGGCATCCGCTTACAGACAAGCTGTGACCGTCTCCGGAG

CTGCATGTGTCAGAGGTTTTCACCGTCATCACCGAAACGCGCGAGACGAAAGGGCC

TCGTGATACGCCTATTTTTATAGGTTAATGTCATGATAATAATGGTTTCTTAGACGTC

AGGTGGCACTTTTCGGGGAAATGTGCGCGGAACCCCTATTTGTTTATTTTTCTAAATA

CATTCAAATATGTATCCGCTCATGAGACAATAACCCTGATAAATGCTTCAATAATAT

TGAAAAAGGAAGAGTATGAGTATTCAACATTTCCGTGTCGCCCTTATTCCCTTTTTTG

CGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGT

AAGATCCTTGAGAGTTTTCGCCCCGAAGAACGTTTTCCAATGATGAGCACTTTTAAA

GTTCTGCTATGTGGCGCGGTATTATCCCGTATTGACGCCGGGCAAGAGCAACTCGGT

CGCCGCATACACTATTCTCAGAATGACTTGGTTGAGTACTCACCAGTCACAGAAAAG

CATCTTACGGATGGCATGACAGTAAGAGAATTATGCAGTGCTGCCATAACCATGAGT

GATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGA

GCTGAATGAAGCCATACCAAACGACGAGCGTGACACCACGATGCCTGTAGCAATGG

CAACAACGTTGCGCAAACTATTAACTGGCGAACTACTTACTCTAGCTTCCCGGCAAC

AATTAATAGACTGGATGGAGGCGGATAAAGTTGCAGGACCACTTCTGCGCTCGGCC

CTTCCGGCTGGCTGGTTTATTGCTGATAAATCTGGAGCCGGTGAGCGTGGGTCTCGC

GGTATCATTGCAGCACTGGGGCCAGATGGTAAGCCCTCCCGTATCGTAGTTATCTAC

ACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTA

GATTGATTTAAAACTTCATTTTTAATTTAAAAGGATCTAGGTGAAGATCCTTTTTGAT

AATCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCTGCT

TGCAAACAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTACA

TACCTCGCTCTGCTAATCCTGTTACCAGTGGCTGCTGCCAGTGGCGATAAGTCGTGT

CTTACCGGGTTGGACTCAAGACGATAGTTACCGGATAAGGCGCAGCGGTCGGGCTG

AACGGGGGGTTCGTGCACACAGCCCAGCTTGGAGCGAACGACCTACACCGAACTGA

GATACCTACAGCGTGAGCTATGAGAAAGCGCCACGCTTCCCGAAGGGAGAAAGGCG

GACAGGTATCCGGTAAGCGGCAGGGTCGGAACAGGAGAGCGCACGAGGGAGCTTC

CAGGGGGAAACGCCTGGTATCTTTATAGTCCTGTCGGGTTTCGCCACCTCTGACTTG

AGCGTCGATTTTTGTGATGCTCGTCAGGGGGCGGAGCCTATGGAAAAACGCCAGC

AACGCGGCCTTTTTACGGTTCCTGGCCTTTTGCTGGCCTTTTGCTCACATGTTCTTTCC

TGCGTTATCCCCTGATTCTGTGGATAACCGTATTACCGCCTTTGAGTGAGCTGATACC

GCTCGCCGCAGCCGAACGACCGAGCGCAGCGAGTCAGTGAGCGAGGAAGCGGAAG
```

-continued
```
AGCGCCCAATACGCAAACCGCCTCTCCCCGCGCGTTGGCCGATTCATTAATGCAGCT

GCGCGCTCGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGCCAACTCC

ATCACTAGGGGTTCCTTGTAGTTAATGATTAACCCGCCATGCTACTTATCTACGTAGC

CATGCTCTAGGACATTGATTATTGACTAGTGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGT

ATTTACGGTAAACTGCCCACTTGGCAGTACATCAAGTGTATCATATGCCAAGTACGC

CCCCTATTGACGTCAATGACGGTAAATGGCCCGCCTGGCATTATGCCCAGTACATGA

CCTTATGGGACTTTCCTACTTGGCAGTACATCTACGTATTAGTCATCGCTATTACCAT

GGTCGAGGTGAGCCCCACGTTCTGCTTCACTCTCCCCATCTCCCCCCCCTCCCCACCC

CCAATTTTGTATTTATTTATTTTTAATTATTTTGTGCAGCGATGGGGGCGGGGGGG

GGGGGGGCGCGCCAGGCGGGGCGGGGCGGGGCGAGGGGGGGGGGGCGAG

GCGGAGAGGTGCGGCGGCAGCCAATCAGAGCGGCGCGCTCCGAAAGTTTCCTTTTA

TGGCGAGGCGGCGGCGGCGGCGGCCCTATAAAAAGCGAAGCGCGCGGCGGGCGGG

AGTCGCTGCGCGCTGCCTTCGCCCCGTGCCCCGCTCCGCCGCCGCCTCGCGCCGCCC

GCCCCGGCTCTGACTGACCGCGTTACTAAAACAGGTAAGTCCGGCCTCCGCGCCGG

GTTTTGGCGCCTCCCGCGGGCGCCCCCCTCCTCACGGCGAGCGCTGCCACGTCAGAC

GAAGGGCGCAGCGAGCGTCCTGATCCTTCCGCCCGGACGCTCAGGACAGCGGCCCG

CTGCTCATAAGACTCGGCCTTAGAACCCCAGTATCAGCAGAAGGACATTTTAGGACG

GGACTTGGGTGACTCTAGGGCACTGGTTTTCTTTCCAGAGAGCGGAACAGGCGAGG

AAAAGTAGTCCCTTCTCGGCGATTCTGCGGAGGGATCTCCGTGGGGCGGTGAACGCC

GATGATGCCTCTACTAACCATGTTCATGTTTTCTTTTTTTTTCTACAGGTCCTGGGTG

ACGAACAGGGTACC
```

3'

SEQ ID NO. 2 (mRNA expression cassette No. 2 - TLR9).
5'

```
GCCACCATGGGCTTCTGCAGAAGCGCCTTGCACCCTCTGAGTCTCCTGGTGCAGGCT

ATCATGCTGGCCATGACCCTTGCCCTGGGCACACTGCCAGCTTTCTTGCCTTGCGAG

CTGCAGCCTCACGGACTGGTCAACTGTAATTGGCTGTTCCTGAAGAGCGTGCCTCAC

TTTTCTATGGCCGCCCCTAGAGGCAACGTGACATCTCTAAGCCTGAGCAGCAACCGG

ATTCACCATCTGCACGACAGCGACTTCGCCCACCTGCCTTCTCTGCGCCACTTGAAC

CTGAAATGGAACTGCCCCCCCGTGGGCCTGAGCCCAATGCACTTTCCTTGTCACATG

ACCATCGAACCTAGCACCTTTCTGGCTGTTCCTACCCTGGAAGAACTGAACCTGAGC

TACAATAACATCATGACAGTGCCTGCCCTGCCAAAGAGCCTGATCAGCCTGTCCTTA

TCTCACACCAACATCCTGATGCTAGATAGCGCTAGCCTGGCTGGACTGCATGCCCTG

AGATTCCTGTTCATGGACGGCAACTGCTACTACAAGAACCCCTGTAGACAGGCACTG

GAGGTGGCCCCTGGAGCCCTGCTGGGCCTTGGCAATCTGACCCACCTGAGCCTGAA

GTACAACAACCTGACAGTGGTGCCTCGGAATCTCCCCAGCTCCCTTGAGTACCTGCT

CCTGAGCTACAACAGAATCGTGAAGTTGGCCCCTGAGGATCTGGCCAACCTTACCGC
```

-continued

```
CCTGCGGGTGCTGGACGTGGGAGGCAACTGCAGACGGTGCGACCACGCCCCTAACC
CTTGCATGGAATGCCCTAGACACTTCCCCCAGCTGCACCCTGACACATTCAGCCATC
TGAGCAGACTGGAAGGCCTGGTGCTGAAGGACAGCAGCCTGTCTTGGCTGAACGCC
AGCTGGTTCAGAGGACTCGGCAACCTGCGGGTTCTGGATCTGAGCGAGAACTTCCTG
TATAAATGCATCACCAAGACCAAGGCCTTTCAGGGCCTGACACAGCTGAGAAAGCT
GAACCTGAGCTTCAACTACCAGAAAGAGTGAGCTTTGCCCACCTGTCCCTGGCGCC
TTCCTTTGGCTCTCTGGTGGCCCTGAAAGAACTGGACATGCACGGCATCTTCTTCAG
AAGCCTCGATGAAACCACCCTGAGACCTCTCGCAAGACTGCCCATGCTGCAAACAC
TGAGGCTGCAGATGAACTTCATCAACCAGGCTCAGCTGGGAATCTTCAGAGCCTTCC
CCGGCCTCAGATACGTGGACCTGAGTGACAACCGGATCAGCGGCGCCTCCGAGCTG
ACCGCCACCATGGGAGAAGCCGATGGCGGCGAGAAGGTGTGGCTGCAGCCTGGCGA
TTTGGCTCCTGCCCCTGTGGACACCCCAAGCTCTGAGGATTTTCGACCTAATTGCAG
CACCCTGAACTTCACCCTGGACCTTTCTCGGAACAACCTGGTTACAGTGCAACCTGA
AATGTTCGCCCAGCTGAGCCACCTGCAGTGCCTGCGGCTGAGCCACAATTGTATCAG
CCAGGCTGTGAACGGTTCCCAATTTCTGCCACTGACCGGCCTGCAGGTGCTGGATCT
CTCTCACAATAAGCTGGATCTGTACCACGAGCACAGCTTTACAGAGCTACCCCGGCT
GGAGGCCCTGGATCTGAGCTATAACAGCCAACCTTTCGGCATGCAGGGCGTGGGCC
ACAACTTCTCTTTCGTGGCCCACCTGAGAACCCTGAGACACTTATCCCTGGCTCATA
ACAACATCCACAGCCAGGTGTCCCAACAGCTGTGCAGCACATCCCTCAGAGCCCTG
GACTTCTCCGGCAACGCCTTAGGTCATATGTGGGCCGAGGGCGATCTGTACCTGCAC
TTCTTCCAGGGCCTGAGCGGGCTGATCTGGCTGGACTTAAGCCAGAACAGACTGCAC
ACACTGCTGCCACAGACCCTGAGAAACCTGCCTAAGTCCCTGCAGGTCCTTAGGCTG
AGAGACAATTACCTGGCATTCTTCAAGTGGTGGTCCCTCCACTTCCTGCCCAAGCTG
GAGGTTCTCGACCTGGCCGGCAACCAGCTGAAAGCCCTGACCAACGGCAGCCTGCC
CGCTGGCACCAGACTGCGGCGGCTCGACGTGAGCTGCAACAGTATTTCTTTCGTGGC
CCCCGGATTCTTTAGCAAGGCCAAAGAGCTGAGGGAACTGAATCTGTCTGCCAACG
CCCTGAAGACCGTTGATCACAGCTGGTTCGGACCTCTGGCCAGCGCCCTGCAAATCC
TGGACGTGAGCGCCAATCCCCTTCACTGCGCCTGCGGCGCCGCATTTATGGACTTCC
TACTGGAGGTGCAGGCCGCCGTGCCTGGCCTTCCTAGCCGGGTCAAGTGCGGCAGC
CCTGGCCAGCTGCAAGGACTCTCCATCTTCGCTCAGGACCTGCGCCTGTGTCTGGAC
GAGGCCCTGTCTTGGGATTGCTTCGCCCTGTCACTGCTGGCGGTGGCCCTGGGCCTG
GGCGTGCCCATGCTGCATCACCTGTGTGGTTGGGACCTGTGGTACTGCTTCCACCTG
TGCCTCGCTTGGCTGCCTTGGCGGGAAGACAGAGCGGCAGAGACGAGGACGCCCT
GCCATACGACGCCTTTGTGGTGTTCGACAAGACCCAGAGCGCCGTGGCCGACTGGG
TGTATAACGAGCTGAGGGGCCAGCTCGAAGAGTGTAGAGGCCGGTGGGCTCTGCGT
CTGTGCCTTGAGGAAAGAGACTGGCTGCCCGGCAAGACACTTTTCGAGAACTTGTGG
GCCAGCGTGTACGGCAGCAGAAAGACCCTGTTCGTGCTGGCCCACACTGATAGAGT
GAGCGGCCTGCTGCGGGCCAGCTTTCTGCTCGCTCAGCAGCGGCTGCTGGAAGACA
GAAAGGACGTGGTTGTGCTTGTGATCCTGAGCCCTGACGGCAGAAGAAGCCGGTAC
GTGCGGCTGAGACAGAGACTGTGTAGACAGTCTGTGTTGCTGTGGCCCCACCAGCCC
```

-continued

AGCGGACAGAGATCCTTCTGGGCCCAACTGGGCATGGCTCTGACCAGAGATAACCA

CCACTTCTACAACCGGAATTTCTGCCAGGGCCCTACAGCCGAGTGA

3'

SEQ ID NO. 3 = SEQ ID NO. 1 + SEQ ID NO. 2
5'

TTCTAGAAAGATCTAACTTGTTTATTGCAGCTTATAATGGTTACAAATAAAGCAATA

GCATCACAAATTTCACAAATAAAGCATTTTTTTCACTGCATTCTAGTTGTGGTTTGTC

CAAACTCATCAATGTATCTTATCATGTCTGGATCTCGACCTCGACTAGAGCATGGCT

ACGTAGATAAGTAGCATGGCGGGTTAATCATTAACTACAAGGAACCCCTAGTGATG

GAGTTGGCCACTCCCTCTCTGCGCGCTCGCTCGCTCACTGAGGCCGGGCGACCAAAG

GTCGCCCGACGCCCGGGCTTTGCCCGGGCGGCCTCAGTGAGCGAGCGAGCGCGCAG

CTGGCGTAATAGCGAAGAGGCCCGCACCGATCGCCCTTCCCAACAGTTGCGCAGCC

TGAATGGCGAATGGCGATTCCGTTGCAATGGCTGGCGGTAATATTGTTCTGGATATT

ACCAGCAAGGCCGATAGTTTGAGTTCTTCTACTCAGGCAAGTGATGTTATTACTAAT

CAAAGAAGTATTGCGACAACGGTTAATTTGCGTGATGGACAGACTCTTTTACTCGGT

GGCCTCACTGATTATAAAAACACTTCTCAGGATTCTGGCGTACCGTTCCTGTCTAAA

ATCCCTTTAATCGGCCTCCTGTTTAGCTCCCGCTCTGATTCTAACGAGGAAAGCACGT

TATACGTGCTCGTCAAAGCAACCATAGTACGCGCCCTGTAGCGGCGCATTAAGCGC

GGCGGGTGTGGTGGTTACGCGCAGCGTGACCGCTACACTTGCCAGCGCCCTAGCGC

CCGCTCCTTTCGCTTTCTTCCCTTCCTTTCTCGCCACGTTCGCCGGCTTTCCCCGTCAA

GCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACG

GTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCC

GATTTCGGCCTATTGGTTAAAAAATGAGCTGATTTAACAAAAATTTAACGCGAATTT

TAACAAAATATTAACGTTTACAATTTAAATATTTGCTTATACAATCTTCCTGTTTTTG

GGGCTTTTCTGATTATCAACCGGGGTACATATGATTGACATGCTAGTTTTACGATTAC

CGTTCATCGATTCTCTTGTTTGCTCCAGACTCTCAGGCAATGACCTGATAGCCTTTGT

AGAGACCTCTCAAAAATAGCTACCCTCTCCGGCATGAATTTATCAGCTAGAACGGTT

GAATATCATATTGATGGTGATTTGACTGTCTCCGGCCTTTCTCACCCGTTTGAATCTT

TACCTACACATTACTCAGGCATTGCATTTAAAATATATGAGGGTTCTAAAAATTTTT

ATCCTTGCGTTGAAATAAAGGCTTCTCCCGCAAAAGTATTACAGGGTCATAATGTTT

TTGGTACAACCGATTTAGCTTTATGCTCTGAGGCTTTATTGCTTAATTTTGCTAATTC

TTTGCCTTGCCTGTATGATTTATTGGATGTTGGAATTCCTGATGCGGTATTTTCTCCTT

ACGCATCTGTGCGGTATTTCACACCGCATATGGTGCACTCTCAGTACAATCTGCTCT

GATGCCGCATAGTTAAGCCAGCCCCGACACCCGCCAACACCCGCTGACGCGCCCTG

ACGGGCTTGTCTGCTCCCGGCATCCGCTTACAGACAAGCTGTGACCGTCTCCGGAG

CTGCATGTGTCAGAGGTTTTCACCGTCATCACCGAAACGCGCGAGACGAAAGGGCC

TCGTGATACGCCTATTTTTATAGGTTAATGTCATGATAATAATGGTTTCTTAGACGTC

AGGTGGCACTTTTCGGGGAAATGTGCGCGGAACCCCTATTTGTTTATTTTTCTAAATA

-continued

```
CATTCAAATATGTATCCGCTCATGAGACAATAACCCTGATAAATGCTTCAATAATAT

TGAAAAAGGAAGAGTATGAGTATTCAACATTTCCGTGTCGCCCTTATTCCCTTTTTG

CGGCATTTTGCCTTCCTGTTTTTGCTCACCCAGAAACGCTGGTGAAAGTAAAAGATG

CTGAAGATCAGTTGGGTGCACGAGTGGGTTACATCGAACTGGATCTCAACAGCGGT

AAGATCCTTGAGAGTTTTCGCCCCGAAGAACGTTTTCCAATGATGAGCACTTTTAAA

GTTCTGCTATGTGGCGCGGTATTATCCCGTATTGACGCCGGGCAAGAGCAACTCGGT

CGCCGCATACACTATTCTCAGAATGACTTGGTTGAGTACTCACCAGTCACAGAAAAG

CATCTTACGGATGGCATGACAGTAAGAGAATTATGCAGTGCTGCCATAACCATGAGT

GATAACACTGCGGCCAACTTACTTCTGACAACGATCGGAGGACCGAAGGAGCTAAC

CGCTTTTTTGCACAACATGGGGGATCATGTAACTCGCCTTGATCGTTGGGAACCGGA

GCTGAATGAAGCCATACCAAACGACGAGCGTGACACCACGATGCCTGTAGCAATGG

CAACAACGTTGCGCAAACTATTAACTGGCGAACTACTTACTCTAGCTTCCCGGCAAC

AATTAATAGACTGGATGGAGGCGGATAAAGTTGCAGGACCACTTCTGCGCTCGGCC

CTTCCGGCTGGCTGGTTTATTGCTGATAAATCTGGAGCCGGTGAGCGTGGGTCTCGC

GGTATCATTGCAGCACTGGGGCCAGATGGTAAGCCCTCCCGTATCGTAGTTATCTAC

ACGACGGGGAGTCAGGCAACTATGGATGAACGAAATAGACAGATCGCTGAGATAG

GTGCCTCACTGATTAAGCATTGGTAACTGTCAGACCAAGTTTACTCATATATACTTTA

GATTGATTTAAAACTTCATTTTTAATTTAAAAGGATCTAGGTGAAGATCCTTTTTGAT

AATCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCTGCT

TGCAAACAAAAAAACCACCGCTACCAGCGGTGGTTTGTTTGCCGGATCAAGAGCTA

CCAACTCTTTTTCCGAAGGTAACTGGCTTCAGCAGAGCGCAGATACCAAATACTGTC

CTTCTAGTGTAGCCGTAGTTAGGCCACCACTTCAAGAACTCTGTAGCACCGCCTACA

TACCTCGCTCTGCTAATCCTGTTACCAGTGGCTGCTGCCAGTGGCGATAAGTCGTGT

CTTACCGGGTTGGACTCAAGACGATAGTTACCGGATAAGGCGCAGCGGTCGGGCTG

AACGGGGGGTTCGTGCACACAGCCCAGCTTGGAGCGAACGACCTACACCGAACTGA

GATACCTACAGCGTGAGCTATGAGAAAGCGCCACGCTTCCCGAAGGGAGAAAGGCG

GACAGGTATCCGGTAAGCGGCAGGGTCGGAACAGGAGAGCGCACGAGGGAGCTTC

CAGGGGGAAACGCCTGGTATCTTTATAGTCCTGTCGGGTTTCGCCACCTCTGACTTG

AGCGTCGATTTTTGTGATGCTCGTCAGGGGGCGGAGCCTATGGAAAAACGCCAGC

AACGCGGCCTTTTTACGGTTCCTGGCCTTTTGCTGGCCTTTTGCTCACATGTTCTTTCC

TGCGTTATCCCCTGATTCTGTGGATAACCGTATTACCGCCTTTGAGTGAGCTGATACC

GCTCGCCGCAGCCGAACGACCGAGCGCAGCGAGTCAGTGAGCGAGGAAGCGGAAG

AGCGCCCAATACGCAAACCGCCTCTCCCCGCGCGTTGGCCGATTCATTAATGCAGCT

GCGCGCTCGCTCGCTCACTGAGGCCGCCCGGGCAAAGCCCGGGCGTCGGGCGACCT

TTGGTCGCCCGGCCTCAGTGAGCGAGCGAGCGCGCAGAGAGGGAGTGGCCAACTCC

ATCACTAGGGGTTCCTTGTAGTTAATGATTAACCCGCCATGCTACTTATCTACGTAGC

CATGCTCTAGGACATTGATTATTGACTAGTGGAGTTCCGCGTTACATAACTTACGGT

AAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGT
```

-continued

```
ATTTACGGTAAACTGCCCACTTGGCAGTACATCAAGTGTATCATATGCCAAGTACGC
CCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCAT
GGTCGAGGTGAGCCCCACGTTCTGCTTCACTCTCCCCATCTCCCCCCCCTCCCCACCC
CCAATTTTGTATTTATTTATTTTTTAATTATTTTGTGCAGCGATGGGGCGGGGGGG
GGGGGGGCGCGCGCCAGGCGGGGCGGGGCGGGGCGAGGGGCGGGGGGGCGAG
GCGGAGAGGTGCGGCGGCAGCCAATCAGAGCGGCGCGCTCCGAAAGTTTCCTTTTA
TGGCGAGGCGGCGGCGGCGGCCCTATAAAAAGCGAAGCGCGCGGCGGGCGGG
AGTCGCTGCGCGCTGCCTTCGCCCCGTGCCCCGCTCCGCCGCCGCCTCGCGCCGCCC
GCCCCGGCTCTGACTGACCGCGTTACTAAAACAGGTAAGTCCGGCCTCCGCGCCGG
GTTTTGGCGCCTCCCGCGGGCGCCCCCCTCCTCACGGCGAGCGCTGCCACGTCAGAC
GAAGGGCGCAGCGAGCGTCCTGATCCTTCCGCCCGGACGCTCAGGACAGCGGCCCG
CTGCTCATAAGACTCGGCCTTAGAACCCCAGTATCAGCAGAAGGACATTTTAGGACG
GGACTTGGGTGACTCTAGGGCACTGGTTTTCTTTCCAGAGAGCGGAACAGGCGAGG
AAAAGTAGTCCCTTCTCGGCGATTCTGCGGAGGGATCTCCGTGGGCGGTGAACGCC
GATGATGCCTCTACTAACCATGTTCATGTTTTCTTTTTTTTCTACAGGTCCTGGGTG
ACGAACAGGGTACCGCCACCATGGGCTTCTGCAGAAGCGCCTTGCACCCTCTGAGTC
TCCTGGTGCAGGCTATCATGCTGGCCATGACCCTTGCCCTGGGCACACTGCCAGCTT
TCTTGCCTTGCGAGCTGCAGCCTCACGGACTGGTCAACTGTAATTGGCTGTTCCTGA
AGAGCGTGCCTCACTTTTCTATGGCCGCCCCTAGAGGCAACGTGACATCTCTAAGCC
TGAGCAGCAACCGGATTCACCATCTGCACGACAGCGACTTCGCCCACCTGCCTTCTC
TGCGCCACTTGAACCTGAAATGGAACTGCCCCCCCGTGGGCCTGAGCCCAATGCACT
TTCCTTGTCACATGACCATCGAACCTAGCACCTTTCTGGCTGTTCCTACCCTGGAAGA
ACTGAACCTGAGCTACAATAACATCATGACAGTGCCTGCCCTGCCAAAGAGCCTGA
TCAGCCTGTCCTTATCTCACACCAACATCCTGATGCTAGATAGCGCTAGCCTGGCTG
GACTGCATGCCCTGAGATTCCTGTTCATGGACGGCAACTGCTACTACAAGAACCCCT
GTAGACAGGCACTGGAGGTGGCCCCTGGAGCCCTGCTGGGCCTTGGCAATCTGACC
CACCTGAGCCTGAAGTACAACAACCTGACAGTGGTGCCTCGGAATCTCCCCAGCTCC
CTTGAGTACCTGCTCCTGAGCTACAACAGAATCGTGAAGTTGGCCCCTGAGGATCTG
GCCAACCTTACCGCCCTGCGGGTGCTGGACGTGGGAGGCAACTGCAGACGGTGCGA
CCACGCCCCTAACCCTTGCATGGAATGCCCTAGACACTTCCCCCAGCTGCACCCTGA
CACATTCAGCCATCTGAGCAGACTGGAAGGCCTGGTGCTGAAGGACAGCAGCCTGT
CTTGGCTGAACGCCAGCTGGTTCAGAGGACTCGGCAACCTGCGGGTTCTGGATCTGA
GCGAGAACTTCCTGTATAAATGCATCACCAAGACCAAGGCCTTTCAGGGCCTGACA
CAGCTGAGAAAGCTGAACCTGAGCTTCAACTACCAGAAAAGAGTGAGCTTTGCCCA
CCTGTCCCTGGCGCCTTCCTTTGGCTCTCTGGTGCCCTGAAAGAACTGGACATGCA
CGGCATCTTCTTCAGAAGCCTCGATGAAACCACCCTGAGACCTCTCGCAAGACTGCC
CATGCTGCAAACACTGAGGCTGCAGATGAACTTCATCAACCAGGCTCAGCTGGGAA
TCTTCAGAGCCTTCCCCGGCCTCAGATACGTGGACCTGAGTGACAACCGGATCAGCG
GCGCCTCCGAGCTGACCGCCACCATGGGAGAAGCCGATGGCGGCGAGAAGGTGTGG
CTGCAGCCTGGCGATTTGGCTCCTGCCCCTGTGGACACCCCAAGCTCTGAGGATTTT
```

-continued

```
CGACCTAATTGCAGCACCCTGAACTTCACCCTGGACCTTTCTCGGAACAACCTGGTT
ACAGTGCAACCTGAAATGTTCGCCCAGCTGAGCCACCTGCAGTGCCTGCGGCTGAG
CCACAATTGTATCAGCCAGGCTGTGAACGGTTCCCAATTTCTGCCACTGACCGGCCT
GCAGGTGCTGGATCTCTCTCACAATAAGCTGGATCTGTACCACGAGCACAGCTTTAC
AGAGCTACCCCGGCTGGAGGCCCTGGATCTGAGCTATAACAGCCAACCTTTCGGCAT
GCAGGGCGTGGGCCACAACTTCTCTTTCGTGGCCCACCTGAGAACCCTGAGACACTT
ATCCCTGGCTCATAACAACATCCACAGCCAGGTGTCCCAACAGCTGTGCAGCACATC
CCTCAGAGCCCTGGACTTCTCCGGCAACGCCTTAGGTCATATGTGGGCCGAGGGCGA
TCTGTACCTGCACTTCTTCCAGGGCCTGAGCGGGCTGATCTGGCTGGACTTAAGCCA
GAACAGACTGCACACACTGCTGCCACAGACCCTGAGAAACCTGCCTAAGTCCCTGC
AGGTCCTTAGGCTGAGAGACAATTACCTGGCATTCTTCAAGTGGTGGTCCCTCCACT
TCCTGCCCAAGCTGGAGGTTCTCGACCTGGCCGGCAACCAGCTGAAAGCCCTGACC
AACGGCAGCCTGCCCGCTGGCACCAGACTGCGGCGGCTCGACGTGAGCTGCAACAG
TATTTCTTTCGTGGCCCCCGGATTCTTTAGCAAGGCCAAAGAGCTGAGGGAACTGAA
TCTGTCTGCCAACGCCCTGAAGACCGTTGATCACAGCTGGTTCGGACCTCTGGCCAG
CGCCCTGCAAATCCTGGACGTGAGCGCCAATCCCCTTCACTGCGCCTGCGGCGCCGC
ATTTATGGACTTCCTACTGGAGGTGCAGGCCGCCGTGCCTGGCCTTCCTAGCCGGGT
CAAGTGCGGCAGCCCTGGCCAGCTGCAAGGACTCTCCATCTTCGCTCAGGACCTGCG
CCTGTGTCTGGACGAGGCCCTGTCTTGGGATTGCTTCGCCCTGTCACTGCTGGCGGT
GGCCCTGGGCCTGGGCGTGCCCATGCTGCATCACCTGTGTGGTTGGGACCTGTGGTA
CTGCTTCCACCTGTGCCTCGCTTGGCTGCCTTGGCGGGAAGACAGAGCGGCAGAG
ACGAGGACGCCCTGCCATACGACGCCTTTGTGGTGTTCGACAAGACCCAGAGCGCC
GTGGCCGACTGGGTGTATAACGAGCTGAGGGGCCAGCTCGAAGAGTGTAGAGGCCG
GTGGGCTCTGCGTCTGTGCCTTGAGGAAAGAGACTGGCTGCCCGGCAAGACACTTTT
CGAGAACTTGTGGGCCAGCGTGTACGGCAGCAGAAAGACCCTGTTCGTGCTGGCCC
ACACTGATAGAGTGAGCGGCCTGCTGCGGGCCAGCTTTCTGCTCGCTCAGCAGCGGC
TGCTGGAAGACAGAAAGGACGTGGTTGTGCTTGTGATCCTGAGCCCTGACGGCAGA
AGAAGCCGGTACGTGCGGCTGAGACAGAGACTGTGTAGACAGTCTGTGTTGCTGTG
GCCCCACCAGCCCAGCGGACAGAGATCCTTCTGGGCCCAACTGGGCATGGCTCTGA
CCAGAGATAACCACCACTTCTACAACCGGAATTTCTGCCAGGGCCCTACAGCCGAGT
GA
```

3'

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3 or at the 5' end of SEQ ID NO. 1.

As will be appreciated by those skilled in the art, a perfect match of nucleotides with each of the expression cassette sequences is not necessary in order to have the desired result of increased bioavailability of the target biomolecule as a result of the target cell mRNA of the target biomolecule. In some embodiments of the present disclosure, about 80% to about 100% nucleotide sequence matching with each of the mRNA expression cassettes causes the desired result. In some embodiments of the present disclosure, about 85% to about 100% nucleotide sequence matching with each of the mRNA expression cassettes causes the desired result. In some embodiments of the present disclosure, about 90% to about 100% nucleotide sequence matching with each of the mRNA expression cassettes causes the desired result. In some embodiments of the present disclosure, about 95% to about 100% nucleotide sequence matching with each of the mRNA expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mRNA expression cassette was amplified by polymerase chain reaction (PCR) using Taq polymerase and the PCR products were gel purified and the bands on interest were also excised and purified using a gel extraction kit. These PCR products contained the mRNA expression cassettes in addition to 15 base pair 5' and 3' overhangs that aligned with the ends of the linearized pAVA-00200 backbone. Using in-fusion cloning, the amplified mRNA expression cassettes are integrated with the pAVA-00200 backbone via homologous recombination. The resulting RP contained the following: 5' ITR, CASI promoter, mRNA expression cassette, WPRE, SV40 polyA and ITR 3'.

The invention claimed is:

1. A composition that comprises a recombinant plasmid (RP) with a sequence of nucleotides that comprise a start region, an end region and an insert positioned between the start region and the end region, in which the insert encodes for a sequence of messenger ribonucleic acid (mRNA) that encodes for a protein, wherein the insert comprises 95% to 100% of the same nucleotide sequence as SEQ ID NO. 2.

2. The composition of claim 1, wherein the sequence of nucleotides is configured to be delivered to a target cell that has an under-expressed or mis-expressed the protein, wherein the sequence of nucleotides is encased in a protein coat, a lipid vesicle, or any combination thereof.

3. The composition of claim 1, wherein the sequence of nucleotides is configured to be delivered to a target cell that has an under-expressed or mis-expressed biomolecule, wherein the sequence of nucleotides is encased in a viral vector.

4. The composition of claim 3, wherein the viral vector is one of a double stranded DNA virus, a single stranded DNA virus, a single stranded RNA virus, or a double stranded RNA virus.

5. The composition of claim 4, wherein the viral vector is an adeno-associated virus.

6. A composition that comprises a recombinant plasmid (RP) with a sequence of nucleotides for encoding a sequence of messenger ribonucleic acid (mRNA) that that encodes for a protein, wherein the sequence is SEQ ID NO. 3.

* * * * *